United States Patent [19]

Sawai et al.

[11] Patent Number: 5,041,429
[45] Date of Patent: Aug. 20, 1991

[54] CELL ACTIVATORS, CIRCULATORY AMELIORATORS AND EDIBLE COMPOSITIONS

[75] Inventors: Kiichi Sawai, Funabashi; Masayasu Kurono, Mie; Hiromoto Asai, Nagoya; Takahiko Mitani, Mie; Motohide Hayashi, Uto; Tunematu Suzuki, Kumamoto; Naohisa Ninomiya, Nagoya, all of Japan

[73] Assignee: Sanwa Kagaku Kenkyusho Co., Ltd., Aichi, Japan

[21] Appl. No.: 354,553

[22] Filed: May 22, 1989

[30] Foreign Application Priority Data

Jun. 1, 1988 [JP] Japan .................................. 63-132768
Jun. 1, 1988 [JP] Japan .................................. 63-132769

[51] Int. Cl.$^5$ .............................................. A61K 31/66
[52] U.S. Cl. .................................... 514/143; 424/439; 424/440; 558/156; 558/161
[58] Field of Search ................. 514/143; 558/156, 161; 424/439, 440

[56] References Cited

U.S. PATENT DOCUMENTS 2,170,274  8/1939  Morgan ............................... 558/161
4,473,563  9/1984  Nicolau et al. ...................... 514/143
4,758,430  7/1988  Sabin ..................................... 514/23

OTHER PUBLICATIONS

Merck Manual (Merck and Co., Rahway, NJ 1987) pp. 1336–1337.

Primary Examiner—Mukund J. Shah
Assistant Examiner—E. C. Ward
Attorney, Agent, or Firm—Armstrong, Nikaido, Marmelstein, Kubovcik & Murray

[57] ABSTRACT

Phytic acid or at least one of its salts is used as an effective component for cell activators in a hypoxic state, circulatory ameliorators, dementia remedies and edible compositions.

1 Claim, 3 Drawing Sheets

CELL ACTIVATORS, CIRCULATORY AMELIORATORS AND EDIBLE COMPOSITIONS

BACKGROUND OF THE INVENTION

1. Field of the Invention

The present invention relates to a cell activator in a hypoxic state, which contains as an effective component phytic acid or at least one of its salts and the use thereof.

Thus, the compositions according to the present invention may be used as circulatory ameliorators and dementia remedies since, due to its erythrocytic oxygen dissociation function, phytic acid serves to activate cells in a hypoxic state, and may potentially be employed to treat and prevent various diseases attributed to the regression of circulatory functions, for instance, histionic cell dysfunctions such as cerebral circulation dysfunctions and cardiac tissue dysfunctions as well as frostbite and necrosis.

2. Statement of the Prior Art

Pharmaceutical preparations based on xanthine, pyridine, nicotinic acid, rutin and vitamines have generally been used as circulatory ameliorators.

On the other hand, phytic acids widely appear in plants as calcium and magnesium salts, sometimes a potassium salt. For instance, rice bran contains as high as 9.5 to 14.5% of phytic acid, and provides a starting material for commercial phytic acid and myoinositol derived therefrom.

Phytic acid and its salt have been used in wide applications; in pharmaceutical applications, calcium phytate has been used as a calcium enhancement, rice bran itself and sodium phytate as a preventive for calcium calculuses, and potassium phytate for the treatment of hypercalcemia and hypercalciurea in sarcoidosis patients. They have also been utilized in various other fields as fermentative aids for brewing sake and wine, metal removers making use of the chelating action of phytic acid, antioxidants in the presence of iron and calcium ions and anticorrosives for metals.

However, it has not been reported until now that phytic acid and its salts may be used as remedies and preventives for various diseases attributed to circulatory dysfunctions.

Surprisingly, the inventors have now discovered that when orally administered in the process of nutrition experiments, phytic acid shows a detoxifying action and, moreover, serves to activate cells in a hypoxic state due to its erythrocytic oxygen dissociation function.

SUMMARY OF THE INVENTION

In view of the aforesaid findings, the present invention provides a pharmaceutical composition containing phytic acid or at least one of its salts as an active component, which is used as cell activators, circulatory ameliorators and dementia remedies in a hypoxic state as well as an edible composition having such functions.

DETAILED DESCRIPTION OF THE INVENTION

Figure 1:
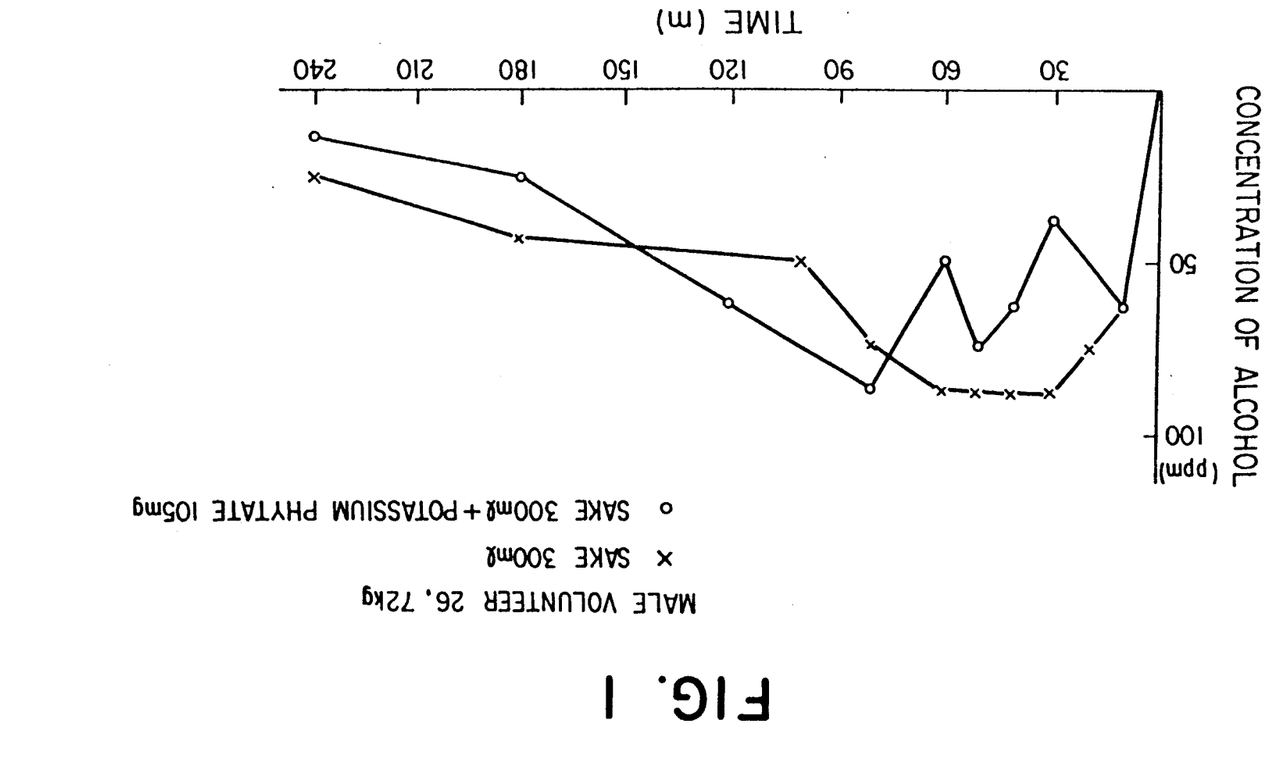
FIGS. 1-3 are graphs illustrating the time-dependent changes in the blood alcohol level of three volunteers upon consumption of either sake alone or sake containing potassium phytate.
Figure 2:
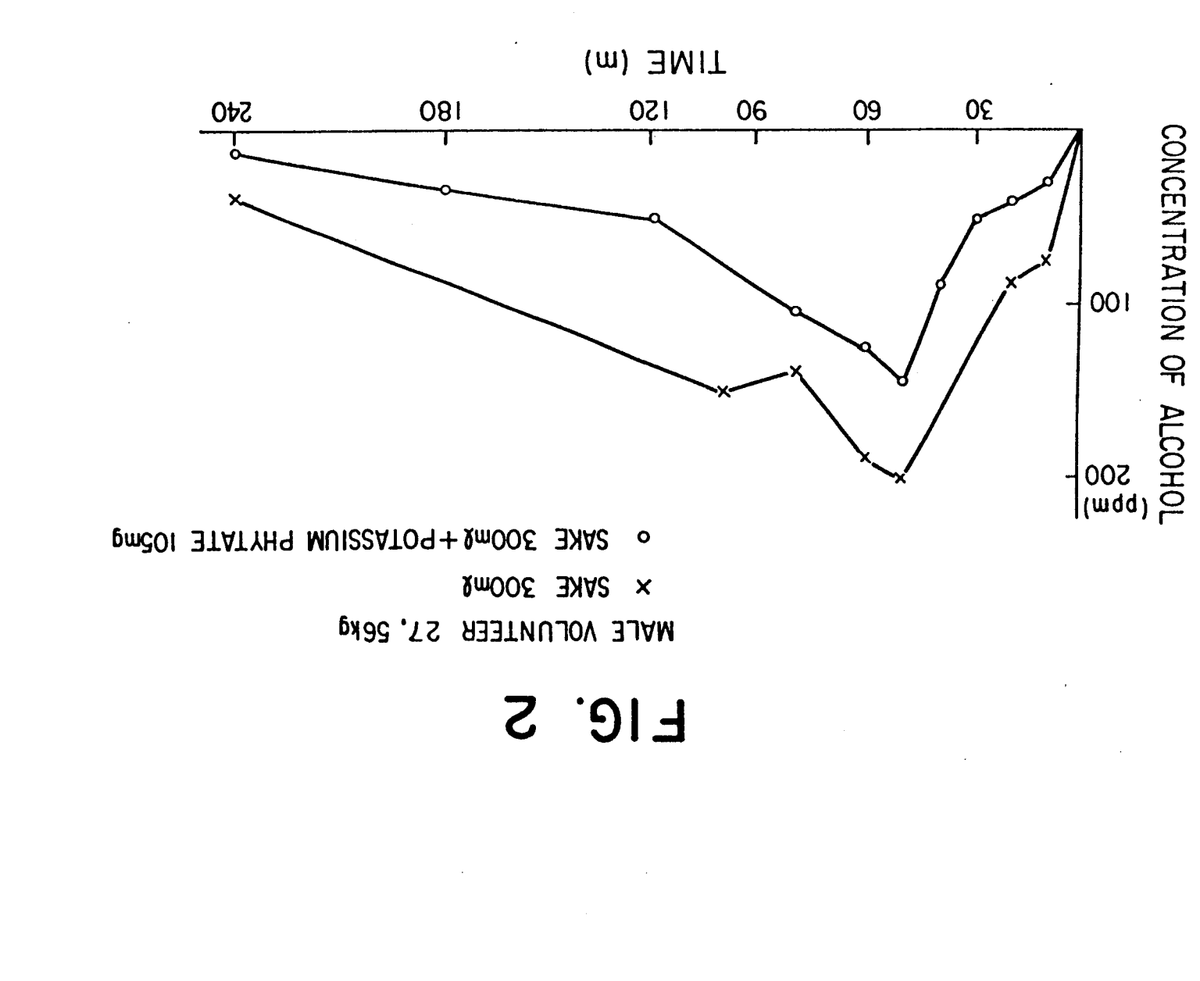
Figure 3:
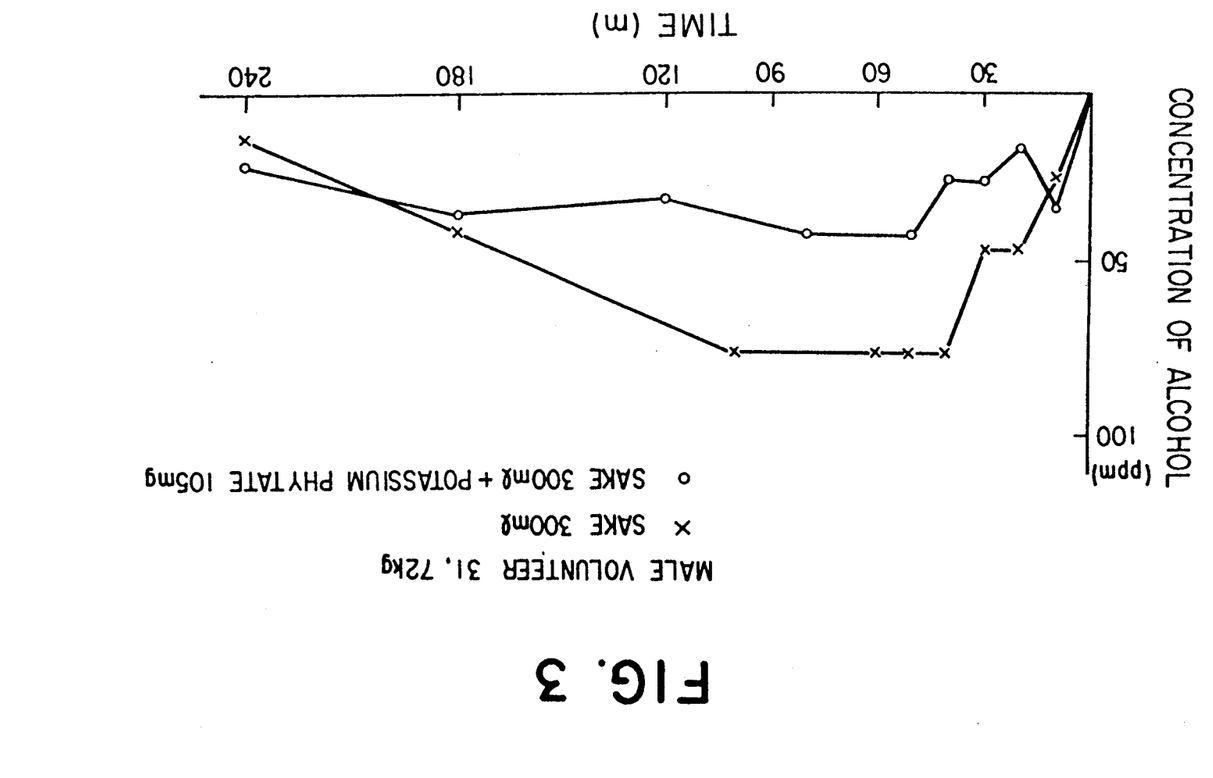

The pharmaceutical and edible compositions according to the present invention are administrable or applicable to both humans and animals.

In various preparations, phytates and their mixtures in a pH range of 6 to 8 may generally be selectively used depending upon the purposes of pharmaceutical and edible compositions because of their strong acidity.

The phytates usable in the present invention may include non-toxic metal salts as well as non-toxic salts with organic salts, basic amino acids and organic ester residues such as those represented by potassium phytate, sodium phytate, ammonium phytate, arginine phytate, ornithine phytate, lysine phytate, histidine phytate, monoethanolamine phytate, diethanolamine phytate, triethanolamine phytate and glucamine phytate.

The number of moles of various bases required to regulate one mole of phytic acid to pH 6 to 8 is shown in Table 1.

TABLE 1

| Bases/pH | 6.00 | 7.00 | 8.00 |
|---|---|---|---|
| NaOH | 7.34 | 8.21 | 8.94 |
| KOH | 7.34 | 8.23 | 8.94 |
| LiOH | 7.41 | 8.38 | 9.30 |
| NH$_4$OH | 7.61 | 8.55 | 9.45 |
| HOC$_2$HCH$_2$NH$_2$ | 7.72 | 8.68 | 9.52 |
| (HOCH$_2$CH$_2$)$_2$NH | 7.54 | 8.45 | 9.31 |
| (HOCH$_2$CH$_2$)$_3$N | 7.20 | 8.53 | 12.1 |
| N-Methylglucamine | 7.62 | 8.49 | 9.25 |
| L-Arginine | 7.79 | 8.67 | 9.60 |
| L-Lysine | 8.01 | 8.98 | 10.0 |
| L-Histidine | 11.3 | — | — |

In view of actions and organs, there are diseases attributable to cerebral circulation dysfunctions, cardiac circulation dysfunctions and histionic circulation dysfunctions. In particular, the cerebral circulation dysfunction diseases include dementia, amnesia, cerebral infarction and the like, and the cardiac circulation dysfunction diseases include cardiac dysrhythmia, cardiovascular dysfunctions (angina pectoris) and so on. The histionic circulation dysfunction diseases include cold abscess, burns, frostbite, chilblains and so on. The compositions according to present invention may be used as the remedies and preventives for such diseases, and may find use as pre-treating agents used to activate tissue during dermanaplasty.

When making the preparations of the present invention, phytic acid or its salts may be dissolved in water for direct use. However, they may be powderized with suitable excipients or vehicles, or may be granulated into granules, tablets, etc. and may further be formulated into medicines for external application.

Since phytic acid is a strong acid, it is preferred in view of the sense of taste, etc. that when the compositions of the present invention are prepared primarily for oral administration, various salts of phytic acid are regulated to a pH about 6 to 8 and selectively used alone or in combination as an active component depending upon the intended purpose.

According to the present invention, phytic acid or its salts may be administered by way of the oral route, since they are effective in the form of both liquid and solid.

EXAMPLES

The present invention will now be explained in further detail with reference to the following test and preparation examples.

EXAMPLE 1—TEST EXAMPLES

1. Pharmaceutical and Pharmacological Effect Tests

EXPERIMENTAL MATERIALS (a) Experimental Animals

Use was made of ddy male mice of five-week age.

(b) Drug to be Examined and Their Preparation

Sodium phytate (Lot. M7K7653, Hani Kagaku) in amounts of 200 mg/kg, 100 mg/kg and 50 mg/kg was dissolved in a small amount of physiological saline, which was then regulated a of pH about 7 with dilute hydrochloric acid (confirmed by pH-paper). The solutions were diluted to the respective concentrations of 20 mg/ml, 10 mg/ml and 5 mg/ml with physiological saline and intraperitoneally administrated to the animals in an amount of 10 ml/kg. Intraperitoneally administrated to a control group were 10 ml/kg of physiological saline.

EFFECT TEST 1—PROTECTIVE ACTION ON MICE UNDER HYPOXIC LOAD

Due to its promoted erythrocytic oxygen dissociation function, phytic acid is expected to produce a protective action against various disorders in a hypoxic state. Accordingly, the mice were allowed to inhale a carbon dioxide gas to determine its influence upon their survival time.

EXPERIMENTAL PROCEDURES

Sixty (60) minutes after the intraperitoneal administration of the drug to be examined, the animals were placed in a desiccator (of 19 cm in diameter and 20 cm in height), and a carbon dioxide gas was then injected thereinto to measure the length of time by the time when the animals died. It is noted that after 30 minutes or 60 minutes of administration, the test and control groups, each of four mice, were simultaneously placed in the desiccators.

In the statistical assay carried out according to the Student's t-test method, the average ± the standard deviation was calculated for each group.

RESULTS AND CONSIDERATIONS

The results of the respective groups are set out in Table 2.

When $CO_2$ was loaded after 30 minutes of administration, there was an increase in the survival time of the test groups to which 50 mg/kg, 100 mg/kg and 200 mg/kg of phytic acid were administrated as compared with the control group, but such an increase was insignificant. When $CO_2$ was loaded after 60 minutes of administration, on the other hand, there was no difference in the survival time between the control group and the test groups to which 50 mg/kg and 100 mg/kg of phytic acid were administrated, but there was a significant increase ($p<0.01$) in the survival time of the test group to which 200 mg/kg of phytic acid were administrated.

As discussed above, it has been found that when $CO_2$ is loaded after 30 minutes of the administration of phytic acid, no influence is produced upon the survival time, but the survival time is noticeably increased when $CO_2$ is loaded after 60 minutes of the administration. Thus, phytic acid has been found to activate cells in a hypoxic state and produce a protective effect against hypoxic disorders.

TABLE 2

Action of Phytic Acid on Survival Time under Hypoxic Load (Inhale of $CO_2$)

| | Dosage (mg/kg i.p.) | n | weight (g) | Survival Time (sec) |
|---|---|---|---|---|
| After 30 min of Administration | | | | |
| Control Group | 10 | 7 | 29.2 ± 0.21 | 385.8 ± 27.34 |
| Test Group | 50 | 7 | 29.7 ± 0.40 | 474.4 ± 45.8 |
| " | 100 | 7 | 29.1 ± 0.21 | 478.3 ± 48.01 |
| " | 200 | 7 | 29.7 ± 0.13 | 455.7 ± 76.59 |
| After 60 min of Administration | | | | |
| Control Group | 10 | 10 | 25.6 ± 0.32 | 372.7 ± 18.82 |
| Test Group | 50 | 10 | 26.0 ± 0.42 | 376.1 ± 16.33 |
| " | 100 | 10 | 26.2 ± 0.29 | 377.4 ± 21.40 |
| " | 200 | 10 | 25.9 ± 0.66 | 556.4 ± 55.36** |

**$p<0.01$ vs control (Student t-test)

EFFECT TEST 2—ACTION ON ERYTHRODEGENERATION IN MICE

In order to clarify on how phytic acid, known to have an erythrocytic oxygen dissociation function, acts on erythrodegeneration, tests were carried out in vitro with the red blood cells of rats according to the filtration pressure method.

EXPERIMENTAL PROCEDURES

An erythrocytic suspension was incubated at 37° C. for 5 minutes and then cooled down to room temperature. With a suspended injector (of the 2ch type, manufactured by Natsume Seisakusho), the suspension was passed at a rate of 5 ml/min through a Millibore membrane (SMWP 013 00, Lot No. N7BU008, manufactured by Millibore) having an average diameter of 5 $\mu m$ to record its upstream side pressure on recording paper through a pressure transducer (TP-200TL, manufactured by Nippon Koden).

The filtration pressure was estimated in terms of a pressure increase per min till the lapse of 8 minutes from the commencement of injection, and erythrodegeneration was taken as being influenced when there was a significant difference between the control and test groups, as estimated according to the Student's t-test method.

Phytic acid (in the form of a sodium salt, Lot No. M7K7653, manufactured by Hani Kagaku) was dissolved in physiological saline and regulated to pH 7.0 with hydrochloric acid. Used as the control was physiological saline containing no phytic acid.

HEMOLYSIS

Fifty (50) $\mu l$ of red blood cells prepared in a similar manner as mentioned above were dissolved in a solution of phytic acid in physiological saline to prepare 5 ml of an erythrocytic suspension containing 1% of phytic acid. The suspension was incubated at 37° C. for 5 minutes and then centrifuged at 3,000 rpm for 10 minutes. The absorbance of the supernate was measured at 540 nm to presume the content of free hemoglobin.

The dissolution of phytic acid and the control were the same as mentioned above.

TEST RESULTS

1. Action upon Erythrodegeneration

As set out in Table 3, no appreciable filtration pressure drop was found at 1 mM of phytic acid (at the final concentration), but a filtration pressure rise was about one half of that of the control group, indicating a significant ($p<0.01$) drop.

2. Hemolysis

As set out in Table 4, even when the (final) concentration of phytic acid was 5 mM, there was no difference in the absorbance of the supernatant fluids between the test and control groups, indicating no sign of hemolysis.

CONSIDERATIONS

Human red blood cells are each in the form of a disc which is about 8 μm in diameter and dented in its central region, and are known to circulate through capillary vessels in varied forms. Accordingly, as one way for helping facilitating the circulation of the blood through histionic circulation regions, esp., microhistionic circulation regions, pentoxifyline has primarily and proposed to enhance erythrodegeneration. Experimentally, the blood may be sucked up through a capillary pipette to count the number of red blood cells contained therein. Alternatively, it is proposed to measure a filtration pressure or count the number of red blood cells filtrated through a membrane including bores each smaller in size than a red blood cell. In the instant testing, the most general and simplest filtration pressure method was used.

As already referred to in the "Test Results", the filtration pressure dropped remarkably when the concentration of phytic acid was 5 mM. This was considered to result from promoted erythrodegeneration, rather than from hemolysis.

Thus, it has been found that phytic acid serves to promote not only the erythrocytic oxygen dissociation function but also erythrodegeneration. This suggests a possibility of transferring oxygen into tissue as well as a possibility of ameliorating microcirculation, particularly, ischemic conditions.

TABLE 3

Action of Phytic Acid on Erythrodegeneration of Mice

| Drug | Concentration | n | Filtration Pressure (mmHg/min) |
|---|---|---|---|
| Control Group | | 6 | 12.4 ± 0.6 |
| Test Group | 1 mM | 3 | 10.1 ± 0.3 |
| " | 5 mM | 3 | 6.0 ± 0.6*** |

***$p<0.01$, compared with the control.

TABLE 4

Hemolysis by Phytic Acid

| Drug | Concentration | n | O. D. (54 nm) |
|---|---|---|---|
| Control Group | | 3 | 0.026 ± 0.006 |
| Test Group | 1 mM | 3 | 0.035 ± 0.002 |
| " | 5 mM | 3 | 0.039 ± 0.003 |

EFFECT TEST EXAMPLE 3—ACTION UPON MOUSE'S AMNESIA

Due to its promoted erythrocytic oxygen dissociation function, phytic acid is expected to produce a protective effect against various disorders. Such a protective effect was studied with a dysmnesia model induced by the loading of a carbon dioxide gas.

EXPERIMENTAL PROCEDURES

The indication used was a single passive avoidance reaction.

1) Acquisition Trial

An animal was placed in a bright chamber of a bright and dark box (comprising a bright chamber and a dark chamber, both being of $15.0 \times 17.5 \times 18.5$ cm and including an inlet/outlet combination of $6.0 \times 6.0$ cm to measure the length of time by the time when the animal walked into the dark chamber (the reaction potential time during acquisition, hereinafter abbreviated as A.T.). From just after the animal walked into the dark chamber, foot shocks of 2.5 mA were continuously applied to the animal through a floor's grid with a shock generator scrambler, manufactured by Astech Co., Ltd., until the animal again walked into the bright chamber. To confirm that the model was obtained, no foot shock was applied to a control group (no-FS + hypoxia).

2) Retention Trial

After 24 hours of the acquisition trial, the animal was again placed in the bright chamber of the bright/dark box to measure the length of time by the time when the animal walked into the dark chamber (the reaction potential time during the retention trial, hereinafter abbreviated as R.T.).

3) Preparation of Dysmnesia Model

Immediately after the acquisition trial, the animal was placed in a desiccator of 19 cm in diameter and 20 cm in height, and a $CO_2$ gas was then injected into the desiccator for 40 to 45 seconds till apnoea. After the animal was removed from the desiccator, artificial aspiration was immdiately tried thereon. The animal was then put back and a home cage. For the confirmation of the model, no $CO_2$ was injected into a control group (FS + no-hypoxia).

4) Administration of Drug

The drug to be examined was introperitoneally administrated to a test group of animals at a dosage of 10 ml/kg before 30 minutes or 60 minutes of the acquisition trial, while 10 ml/kg of physiological saline was intraperitoneally administered to a control group of animals.

5) Statistical Assay

For the animals having R.T. exceeding 360 seconds, the average ± the standard deviation was found for each group assuming that R.T. was 360 seconds, and statistical assay was made according to the Student's t-test method. For the animals having R.T. exceeding 360 seconds, on the other hand, the retention % was calculated assuming that the memory was retained, and both-side assay was made according to Fisher's exact provability method.

RESULTS AND CONSIDERATIONS

The results of the respective groups are set out in Table 5.

Referring to the groups of animals to which phytic acid was administrated before 30 minutes of the acquisition trial, there was no difference in the reaction potential time (A.T.) during the acquisition trial between the control group and the test group to which 50 mg/kg of phytic acid were administrated. However, there was a significant increase in the reaction potential time between the control group and the test groups to which 100 mg/kg and 200 mg/kg of phytic acid were administrated, but that increase was of no significance. Referring on the other hand to the groups to which phytic acid was administered before 60 minutes of the acquisition trial, there was no difference between the control group and the test groups to which 50 mg/kg, 100 mg/kg and 200 mg/kg of phytic acid were administrated. The FS+no-hypoxia control was 64.8±11.1 seconds, while the no-hypoxia control was 44.5±9.1 seconds. In the groups to which phytic acid was administrated before 30 minutes of the acquisition trial, an increase in A.T. was found at a dosage of 100 mg/kg or more but, in the groups to which phytic acid was administrated before 60 minutes, such an increase was not found. After about 30 minutes of the administration, phytic acid had some influence upon the behavior of the animals, but such influence was lost after 60 minutes.

Turning to the groups to which phytic acid was administrated before 30 minutes of the acquisition trial, there was no difference in the reaction potential time (R.T.) during the retention trial between the control group and the test groups to which 50 mg/kg and 100 mg/kg of phytic acid were administrated. Referring to the groups to which phytic acid was administrated before 60 minutes of the retention trial, there was a significant increase ($p < 0.05$) between the control group and the test groups to which 50 mg/kg and 100 mg/kg of phytic acid were administrated, but no difference was found in the test group to which 200 mg/kg of pytic acid were administrated. In the groups to which phytic acid was administrated before 30 minutes, no amelioration of dysmnesia was found at any dosage. Thus, the influence of phytic acid upon the behavior of the animals during the acquisition trial were considered to take part in R.T. In the groups to which phytic acid was administrated before 60 minutes, noticeable amelioration of dysmnesia was found at the dosages of 50 mg/kg and 100 mg/kg, but any amelioration of dysmnesia was not found at the dosage of 200 mg/kg. This implies that phytic acid acts in the Belshave's form.

Due to its promoted erythrocytic oxygen dissociation function, phytic acid serves to enhance the transfer of oxygen into anoxic regions and so histionic disorders due to anoxia. Indeed, phytic acid was found to have an effect upon the amelioration of dysmnesia. It is thus suggested that the promoted erythrocytic oxygen dissociation function is effective for dysmnesia due to hypoxic disorders.

2: Taste Testing

One hundred and eighty (180)-milliliter shots of sake and whisky-and-water containing 0.5 g (100 mg calculated as phytic acid) of the liquid preparation according to Preparation Example 4 were simultaneously provided to two 20-member panels to carry out taste testing for comparing both shots in terms of whether taste and smell are good or bad. The results are set forth in the following table.

|  | Undistinguishable from Phytic Acid-Free Shots | Better than Phytic Acid-Free Shots | Bad |
| --- | --- | --- | --- |
| Taste | 14 | 6 | 0 |
| Smell | 18 | 2 | 0 |

From the above results, it has been found that the preparation according to the present invention tastes good, and is effective as a liquor additive.

EXAMPLE 2

Composition a

Twenty-nine (29) g of sodium hydroxide and a suitable amount of refined water are added to 660 g of phytic acid (as an anhydride) to obtain a liquid regulated to pH 6.

Composition b

Four hundred and twelve (412) g of potassium hydroxide and a suitable amount of refined water are added to 660 g of phytic acid (as an anhydride) to obtain a liquid regulated to pH 6.

Composition c

One hundred and seventy-seven (177) g of lithium hydroxide and a suitable amount of refined water are added to 660 g of phytic acid (as an anhydride) to obtain a liquid regulated to pH 6.

Composition d

Five hundred and eighty-one (581) g of ethanolamine and a suitable amount of refined water are added to 660 g of phytic acid (as an anhydride) to obtain a liquid regulated to pH 8.

Composition e

Nine hundred and seventy-nine (979) g of diethanolamine and a suitable amount of refined water are added to 660 g of phytic acid (as an anhydride) to obtain a liquid regulated to pH 8.

TABLE 5

Action of Phytic Acid on Dysmnesia due to the Inhalation of Carbon Dioxide

|  | Dosage (mg/kg i.p.) | n | A.T. (sec) | R.T. (sec) | R (%) |
| --- | --- | --- | --- | --- | --- |
| Before 30 min |  |  |  |  |  |
| Control Group | 10 | 15 | 37.5 ± 4.9 | 185.0 ± 26.5 | 13 |
| Test Group | 50 | 18 | 38.5 ± 4.6 | 182.9 ± 25.7 | 22 |
| " | 100 | 20 | 8.78 ± 12.4*** | 205.0 ± 26.1 | 25 |
| " | 200 | 17 | 114.8 ± 22.9** | 136.5 ± 30.3 | 17 |
| Before 60 min |  |  |  |  |  |
| Control Group | 10 | 28 | 51.8 ± 9.1 | 189.4 ± 19.2 | 17 |
| Test Group | 50 | 24 | 44.6 ± 6.5 | 255.1 ± 19.4* | 33 |
| " | 100 | 26 | 50.5 ± 5.7 | 258.2 ± 20.6* | 38 |
| " | 200 | 23 | 61.3 ± 8.2 | 204.2 ± 23.7 | 21 |
| Foot Shock + No-Hypoxia |  | 14 | 68.4 ± 11.1 | 360.0 ± 0.0*** | 92+++ |
| No-Foot Shock + Hypoxia |  | 13 | 44.5 ± 9.1 | 50.6 ± 19.7*** | 0+++ |

*$p < 0.05$. $p < 0.01$. *$p < 0.001$ vs its control (Student's t-test). +++$p < 0.001$ vs its control (Fisher's exact provability test).

Composition f

One thousand eight hundred and five (1805) g of triethanolamine and a suitable amount of refined water are added to 660 g of phytic acid (as an anhydride) to obtain a liquid adjusted to pH 8.

Composition g

One thousand six hundred and fifty-seven (1657) g of N-methylglucamine and a suitable amount of refined water are added to 660 g of phytic acid (as an anhydride) to obtain a liquid adjusted to pH 7.

Composition h

One thousand five hundred and ten (1510) g of L-arginine and a suitable amount of refined water are added to 660 g of phytic acid (as an anhydride) to obtain a liquid adjusted to pH 7.

Composition i

One thousand seven hundred and fifty-three (1753) g of L-histidine and a suitable amount of refined water are added to 660 g of phytic acid (as an anhydride) to obtain a liquid adjusted to pH 6.

Composition j

One hundred and sixteen (116) g of sodium hydroxide, 478 g of potassium hydroxide, 6.08 g of potassium chloride (as a dihydrate), 157 g of disodium hydrogen phosphate (as an anhydride) and a suitable amount of refined water are added to 660 g of phytic acid (as an anhydride) to obtain a liquid adjusted to pH 9.

These compositions a to j may be powderized by crystallization or the addition of a vehicle.

These compositions a to j may also be formed into compositions in the form of liquids or powders, from which the preparations may be obtained.

EXAMPLE 3

The composition j obtained in Example 2 was formed into compositions, from which various preparations were obtained.

Composition A for Preparations

Lactose is added to composition j (containing 200 mg of phytic acid) to obtain a total of 1000 mg of a composition.

Composition B for Preparations

Lactose is added to composition j (containing 100 mg of phytic acid) to obtain a total of 1000 mg of a composition.

Composition C for Preparations

Refined water is added to composition j (containing 100 mg of phytic acid) to obtain a total of 1000 mg of a composition.

Composition D

Light silicic anhydride is added to composition j (containing 200 mg of phytic acid), followed by drying, which gives a total of 1000 mg of a composition.

PRODUCTION EXAMPLES OF PREPARATIONS

| Production Example 1 (Elixir) | |
| --- | --- |
| Composition C | 100 g (10 g calculated as phytic acid) |
| Compound orange extract | 24 ml |
| Ethanol | 400 ml |
| Gylcerine | 400 ml |
| Refined water | Total: 1000 ml |

Predetermined amounts of the aforesaid components are uniformly mixed together to obtain a colorless and clear elixir preparation. A five-milliliter dosage of this elixir preparation contains 50 mg of phytic acid.

| Production Example 2 (Capsule) | |
| --- | --- |
| Composition A | 200 mg (40 mg calculated as phytic acid) |
| Lactose | 20 mg |
| Corn starch | 38 mg |
| Magnesium stearate | 2 mg |

Predetermined amounts of the aforesaid components are uniformly mixed together and packed in No. 2 capsules. One such capsule contains 40 mg of phytic acid.

| Production Example 3 (Granule) | |
| --- | --- |
| Composition A | 600 mg (120 mg calculated as phytic acid) |
| Lactose | 140 mg |
| Corn starch | 250 mg |
| Hydroxypropylcellulose | 10 mg |

Predetermined amounts of the aforesaid components are uniformly mixed together, and the mixture is then wet-granulated with water and ethanol into granules. One hundred and twenty (120) mg of phytic acid are contained in a one-gram dosage of such granules.

Production Example 4 (Powder)

The composition A is divided and heat-sealed in aluminium to obtain wrappers each of 1.5 g.

| Production Example 5 (Tablet) | |
| --- | --- |
| Composition A | 100 mg (20 mg calculated as phytic acid) |
| Corn starch | 19 mg |
| Crystalline cellulose | 30 mg |
| Magnesium stearate | 1 mg |

Predetermined amounts of the aforesaid components are uniformly mixed together, and the mixture is then compressed into tablets each of 7 mm in diameter and 150 mg in weight. One such tablet contains 20 mg of phytic acid.

| Production Example 6 (Syrup) | |
| --- | --- |
| Composition C | 50 g (5 g calculated as phytic acid) |
| White sugar | 300 g |
| D-sorbitol (70%) | 250 g |
| Methyl p-oxybenzoate | 0.3 g |
| Propyl p-oxybenzoate | 0.15 g |
| Sodium citrate | 10 g |
| Perfume | 1.5 g |
| Refined water | Total: 1000 ml |

* Predetermined amounts of the aforesaid components are dissolved and mixed together into a colorless and clear syrup. One hundred (100) mg of phytic acid is contained in a twenty-milliliter dosage of this syrup.

| Production Example 7 (Dry syrup) | |
| --- | --- |
| Composition B | 100 mg (10 mg calculated as phytic acid) |
| Sodium citrate | 2.4 mg |
| Citric anyhdride | 2.2 mg |
| Tragacanth powders | 2.7 g |
| White sugar | suitable amount |
| Hydroxypropylcellulose | 3.0 mg |
| Perfume | slight amount |
| Perfume | slight amount |

| Production Example 8 (Troche) | |
| --- | --- |
| Composition A | 100 mg (20 mg calculated as phytic acid) |
| White sugar | 870 mg |
| Lactose | 20 mg |
| Magnesium stearate | 10 mg |

Of the aforesaid components composition A and white sugar are uniformly mixed together in the respective amounts of 100 g and 870 g, and are then wet-granulated with water and ethanol, followed by drying at a temperature of lower than 35° C. Added to the dried product are 20 g of lactose and 10 g of magnesium stearate to obtain troches each of 15 mm in diameter and 1 g in weight. One such troche contains 20 mg of phytic acid.

| Production Example 9 (Candy) | |
| --- | --- |
| Composition B | 100 mg (10 mg calculated as phytic acid) |
| White sugar | 2400 mg |
| Starch syrup | 1500 mg |
| Perfume | slight amount |

Of the aforesaid components, 240 g of white sugar and 150 g of starch syrup are mixed with 100 g of refined water. After melting by heating, the mixture is sieved out for the removal of foreign matters. The resulting liquid is concentrated under pressure with the application of heat for dehydration to prepare a starch syrup dough having a moisture content of 2 to 3% at 130° to 150° C. Added to this dough are 10 g of composition B and a slight amount of perfume, and the product is molded to obtain candies each of 4 g in weight. Each candy contains 10 mg of phytic acid.

| Production Example 10 (Lemonade) | |
| --- | --- |
| Composition C | 3 g (300 mg calculated as phytic acid) |
| Syrup | 2.5 ml |
| Refined water | Total: 30 ml |

Predetermined amounts of the aforesaid components are uniformly mixed together into lemonades. A thirty (30)-milliliter dosage of such limonadas contains 300 mg of phytic acid.

| Production Example 11 (Granule) | |
| --- | --- |
| Composition D | 500 mg (100 mg calculated as phytic acid) |
| Garlic powders | 750 mg |
| Lactose | suitable amount |

Predetermined amounts of the aforesaid components are uniformly mixed together, and are then wet-granulated with water and ethanol into granules. One hundred (100) mg of phytic acid is contained in an 1.5-gram dosage of such granules.

| Production Example 12 (Drinkable Solution) | |
| --- | --- |
| Composition C | 1 g (100 mg calculated as phytic acid) |
| Mel | 0.5 g |
| White sugar | 2.0 g |
| Citric acid | suitable amount |
| Sodium citrate | suitable amount |
| Peppermint | slight amount |
| Refined water | suitable amount |

Predetermined amounts of the aforesaid components were uniformly mixed together into a colorless and clear internal liquid preparation. A thirty (30)-milliliter dosage of this liquid preparation contains 100 mg of phytic acid.

| Production Example 13 (Garlic Flavoring) | |
| --- | --- |
| Composition D | 0.285 g (0.1 g calculated as phytic acid) |
| Avicel (Cellulose microcrystalline) | 0.18 g |
| Garlic powders | 0.75 g |
| Light silicic anhydride | 0.256 g |
| Corn starch | suitable amounts |

Predetermined amounts of the aforesaid components are granulated by a conventional method.

| Production Example 14 (External Application O/W Ointment) | |
| --- | --- |
| Sodium Phytate | 0.5% |
| Liquid Paraffin | 10.5% |
| Butylene Glycol | 5.0% |
| Beeswax | 2.0% |
| Cetyl Alcohol | 4.0% |
| Lanolin | 2.0% |
| Squalane | 30.0% |
| Paraben | 0.2% |
| Polyoxyethylene Monosorbitan Laurate | 2.0% |
| Water | Balance |

The above components were blended together at the specified proportions to prepare an ointment.

STABILITY TESTING

The preparations according to Production Examples 1 to 12 were subjected to stability testing to measure the amount of residual phytic acid. The results are set forth in Table 6.

TABLE 6

Amounts of Residual Phytic Acid in the Stability Testing of the Preparations According to the Production Examples
(% with respect to the specified contents)

| Samples | Storage Vessels | At the beginning of Storage | After 3 weeks at 60° C. |
| --- | --- | --- | --- |
| P. Ex. 1A* | Glass Bottle | 100.5 | 101.2 |
| P. Ex. 2B* | PTP | 101.4 | 99.4 |
| P. Ex. 3C* | Aluminum Wrapper | 100.1 | 100.0 |
| P. Ex. 4D* | " | 100.9 | 102.1 |

TABLE 6-continued

Amounts of Residual Phytic Acid in the Stability Testing of the Preparations According to the Production Examples (% with respect to the specified contents)

| Samples | Storage Vessels | At the beginning of Storage | After 3 weeks at 60° C. |
|---|---|---|---|
| P. Ex. 5E* | PTP | 99.2 | 99.8 |
| P. Ex. 6F* | Glass Bottle | 102.1 | 100.3 |
| P. Ex. 7G* | Aluminum Wrapper | 100.6 | 100.1 |
| P. Ex. 8H* | Aluminum SP | 99.7 | 100.5 |
| P. Ex. 9I* | Aluminum Bag | 99.9 | 99.2 |
| P. Ex. 10J* | Glass Bottle | 102.1 | 100.9 |
| P. Ex. 11K* | Aluminum Wrapper | 100.3 | 100.1 |
| P. Ex. 12L* | Glass Bottle | 100.1 | 99.8 |

A*: Elixir, B*: Capsule, C*: Granule, D*: Powder, E*: Tablet, F*: Syrup, G*: Dry Syrup, H*: Troche, I*: Candy, J*: Limonada, K*: Granule, L*: Drinkable Solution.

What is claimed is:

1. A method for preventing or treating carbon dioxide poisoning in an animal which comprises orally administering to an animal in need of such prevention or treatment an effective amount of phytic acid or a pharmaceutically acceptable salt thereof.

* * * * *